US012629026B2

(12) United States Patent
Martena et al.

(10) Patent No.: US 12,629,026 B2
(45) Date of Patent: May 19, 2026

(54) DEVICE FOR THE DIRECT DETECTION OF PRESSURE VARIATIONS OF A FLUID IN A BODY CAVITY

(71) Applicant: ELECTRONIC SYSTEMS S.P.A., Momo (IT)

(72) Inventors: Florinda Martena, Momo (IT); Stefano Trizzino, Momo (IT)

(73) Assignee: ELECTRONIC SYSTEMS S.P.A., Momo (IT)

( * ) Notice: Subject to any disclaimer, the term of this patent is extended or adjusted under 35 U.S.C. 154(b) by 532 days.

(21) Appl. No.: 18/091,806

(22) Filed: Dec. 30, 2022

(65) Prior Publication Data

US 2023/0210370 A1     Jul. 6, 2023

(30) Foreign Application Priority Data

Dec. 30, 2021     (EP) ..................................... 21218308

(51) Int. Cl.
*A61B 3/16* (2006.01)
*A61B 17/34* (2006.01)
(52) U.S. Cl.
CPC ............ *A61B 3/16* (2013.01); *A61B 17/3421* (2013.01); *A61M 2205/3344* (2013.01)
(58) Field of Classification Search
CPC ....... A61B 3/16; A61B 17/3421; A61B 90/06; A61B 2090/064; A61M 2205/3344; A61F 9/00736
See application file for complete search history.

(56) References Cited

U.S. PATENT DOCUMENTS

| | | | |
|---|---|---|---|
| 4,841,984 | A | 6/1989 | Armeniades et al. |
| 2006/0149194 | A1 | 7/2006 | Conston et al. |
| 2008/0082078 | A1 | 4/2008 | Berlin |
| 2011/0118729 | A1 | 5/2011 | Heeren et al. |
| 2014/0171991 | A1 | 6/2014 | Lee et al. |
| 2014/0194834 | A1 | 7/2014 | Passaglia |
| 2017/0312431 | A1 | 11/2017 | Johnson et al. |

FOREIGN PATENT DOCUMENTS

WO          2016139587 A1     9/2016

OTHER PUBLICATIONS

European Search Report for EP 21 21 8308 dated Jun. 1, 2022, Munich, DE.

*Primary Examiner* — Jeffrey G. Hoekstra
(74) *Attorney, Agent, or Firm* — Ferguson Case Orr Paterson

(57) ABSTRACT

A device for directly detecting pressure variations of a fluid within a body cavity is provided. The device has a pressure transducer, a pressure transmission device extending between a distal tip suitable for partial insertion into the body cavity and a proximal port in direct contact with a sensing surface of the pressure transducer. The distal tip forms an access port that places the pressure transducer outside the body cavity into direct fluid communication with the inside of the body cavity. The pressure transmission device has, between the distal tip and the proximal port, a flexible cannula having a length sufficient to allow anchoring of an intermediate stretch of the flexible cannula and/or the pressure transducer to an anchoring zone distant from the body cavity.

16 Claims, 2 Drawing Sheets

DEVICE FOR THE DIRECT DETECTION OF PRESSURE VARIATIONS OF A FLUID IN A BODY CAVITY

CROSS REFERENCE TO RELATED APPLICATION

This application claims priority to and benefit of European Patent Application No. 21218308.1 filed Dec. 30, 2021, the contents of which are incorporated by reference in their entirety.

FIELD OF THE INVENTION

The present invention relates to the field of minimally invasive surgical procedures and in particular to a detection device capable of directly measuring pressure variations of a fluid within a body cavity, in particular for eye surgery procedures.

BACKGROUND OF THE INVENTION

For example, substantial pressure variations can occur in the treated eye during eye surgical procedures involving eyeball manipulation, fluid infusion, fragmentation, and aspiration of ocular tissues. Clinical studies have shown that in vitrectomy surgical procedures for vitreous body removal, intraocular pressure can vary between 0 and 120 mmHg. Pressure values above 60 mmHg, which corresponds to retinal perfusion pressure, have been reported in phacoemulsification surgical procedures for cataract fragmentation and aspiration. Large pressure variations have also been measured following eyeball manipulation maneuvers in scleral indentation surgical procedures for the treatment of retinal detachment, with peaks of up to 210 mmHg in the case of external pressures applied to the sclera.

The variations in intraocular pressure can increase the risk of intraoperative and postoperative complications, such as expulsive hemorrhage, choroid detachment, and retinal ischemia. Expulsive hemorrhage and choroid detachment can be associated with pressure drops during surgery. Prolonged increases in intraocular pressure, on the other hand, can result in a reduction in vascular perfusion pressure with consequent impairment of blood flow to the optic nerve and retina. Pressure variations can also adversely affect visual function recovery after the surgical procedure. Indeed, it has been shown that transient increases in ocular perfusion pressure can lead to morphological and functional alterations in the retina. The effects of variations in intraocular pressure on visual acuity can be particularly detrimental to patients with impaired ocular perfusion, e.g., caused by diabetic retinopathy.

Several devices and methods for measuring intraocular pressure have been suggested.

U.S. Pat. No. 4,841,984 describes a device which relies on direct measurement of intraocular pressure using a pressure transducer integrated on the surgical instrument inserted into the ocular cavity, which is used for fluid infusion or fragmentation and removal of ocular tissue. A control circuit is also present which automatically adjusts the infusion or aspiration of the instrument in response to the measured intraocular pressure, keeping it within the safe range. A first limitation of such a device is the need for a larger ocular incision for the insertion of the instrument and the integrated transducer. A further disadvantage is the proximity of the transducer to the surgical instrument, the operations of which inevitably lead to disturbances and inaccuracies in intraocular pressure measurement.

US 20110118729 A1 describes a vitrectome coupled to a control circuit to enable or disable the instrument based on the measured physical parameter. These parameters can include intraocular pressure, which is used to check whether the vitrectome is positioned correctly within the eye socket. Indeed, to activate the vitrectome, the measured pressure must be equal to the fluid infusion pressure but there is no control over pressure variations relative to the set pressure.

US 20140171991 A1 describes a vitrectome equipped instead with a pressure transducer to monitor the output pressure of the cutting instrument but no direct monitoring of intraocular pressure is performed.

US 2014194834 A1 describes a device for controlling the pressure in the eye consisting four elements: a positioning cannula (housed in the anterior chamber of the eye), a two-way pump (infusion/aspiration), a control circuit, and a pressure sensor housed in the pump reservoir to measure the pressure of the fluid in the reservoir. This device is thus equipped with an indirect measurement system, which allows the measurement of intraocular pressure only in presence of infusion or aspiration of fluid. This system does not allow the measurement of pressure variations caused by external factors or eyeball manipulation.

US 2006/149194 describes a system for treating eye diseases comprising a micro-cannula in which an internal element, configured to exit the distal end of the micro-cannula, can be slidably inserted. The internal element can be used to carry fluids or sensors.

US 2008/0082078 A1 describes a surgical assembly for treating glaucoma comprising a laser configured to produce an ablation beam of a region of a trabecular meshwork of the eye and a delivery system configured to direct the laser beam from within the eye to the trabecular meshwork of the eye, wherein the delivery system can include pressure detection circuitry to detect and control pressure at the surgical site.

WO2016139587A1 describes a surgical assembly for ophthalmic surgical procedures, comprising an optical fiber pressure transducer coupled to a surgical accessory, such as an endoilluminator or infusion cannula, to be jointly inserted into the ocular cavity through an ocular accessory incision.

The monitoring of the pressure variations of a fluid during a surgical procedure is thus of fundamental importance to ensure the safety and effectiveness of the surgical procedure.

SUMMARY OF THE INVENTION

It is the object of the present invention to provide a device that makes it possible to reliably and rapidly detect pressure variations of a fluid, without suffering from the drawbacks of known devices.

It is another object of the present invention to provide a device for the direct detection of the pressure of a fluid, which is particularly convenient for the operator and immune from the disturbances associated with the environmental conditions in which the measurement is made.

It is a further object of the present invention is to limit the number of incisions and minimize the size of the incisions, to make direct pressure detection less invasive and more tolerable for the patient.

Said purposes are achieved with a device for detecting the pressure changes of a fluid in a body cavity as described and claimed herein. Preferred embodiments of the present invention are also described.

BRIEF DESCRIPTION OF THE FIGURES

The features and advantages of the device according to the present invention will be apparent from the description given below of its preferred embodiment examples, given by way of indicative and non-limiting example, with reference to the accompanying figures, in which.

DETAILED DESCRIPTION

Figures 1, 2, 3:
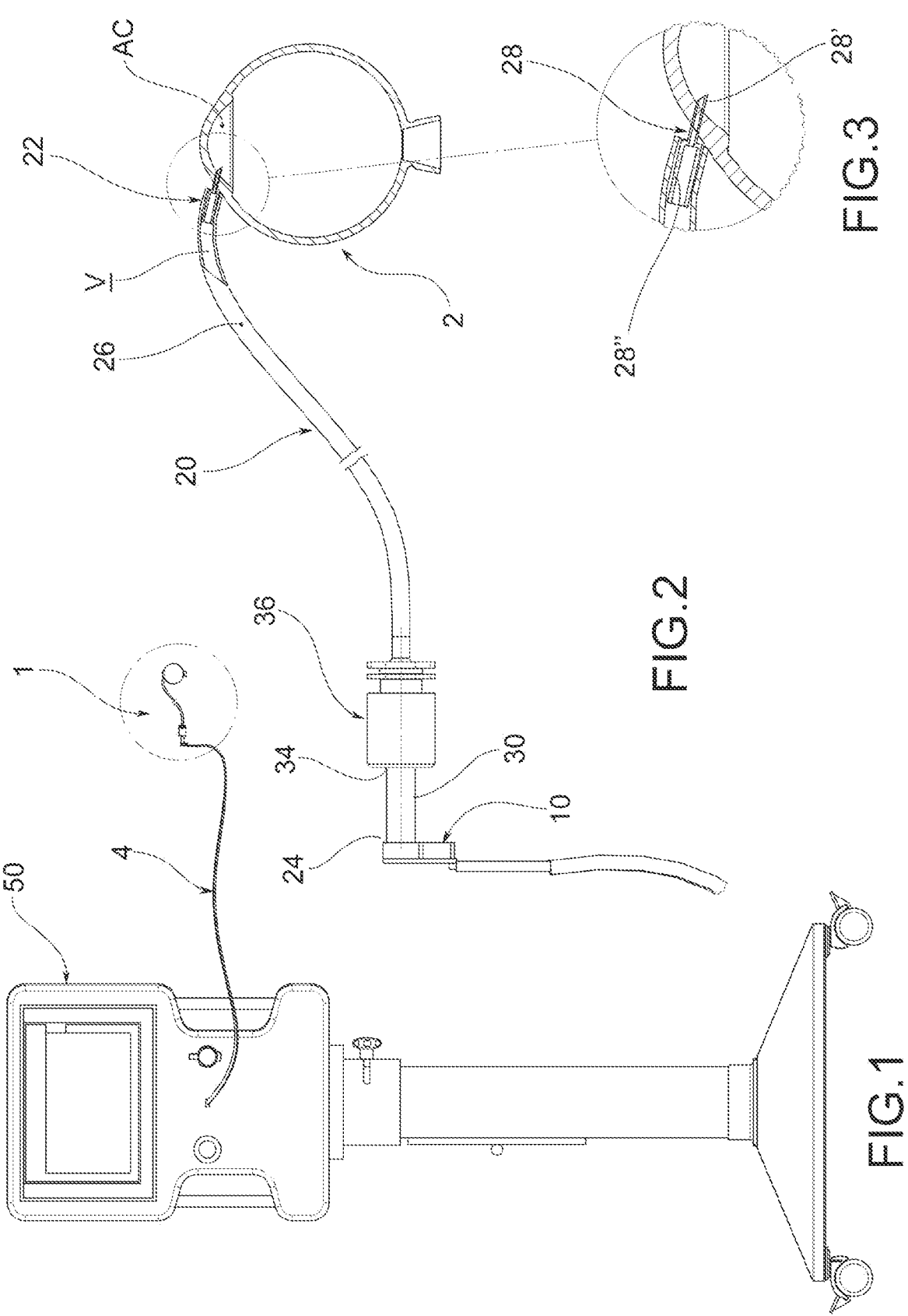
FIG. 1 shows the layout of a direct pressure detection device in an embodiment of the present invention suited for use in cataract surgery, connected to an electronic control unit.
FIG. 2 is an enlarged, partial section view of the portion in the circle in FIG. 1.
FIG. 3 is an enlarged view of the portion in the circle in FIG. 2.
Figures 4, 5, 6:
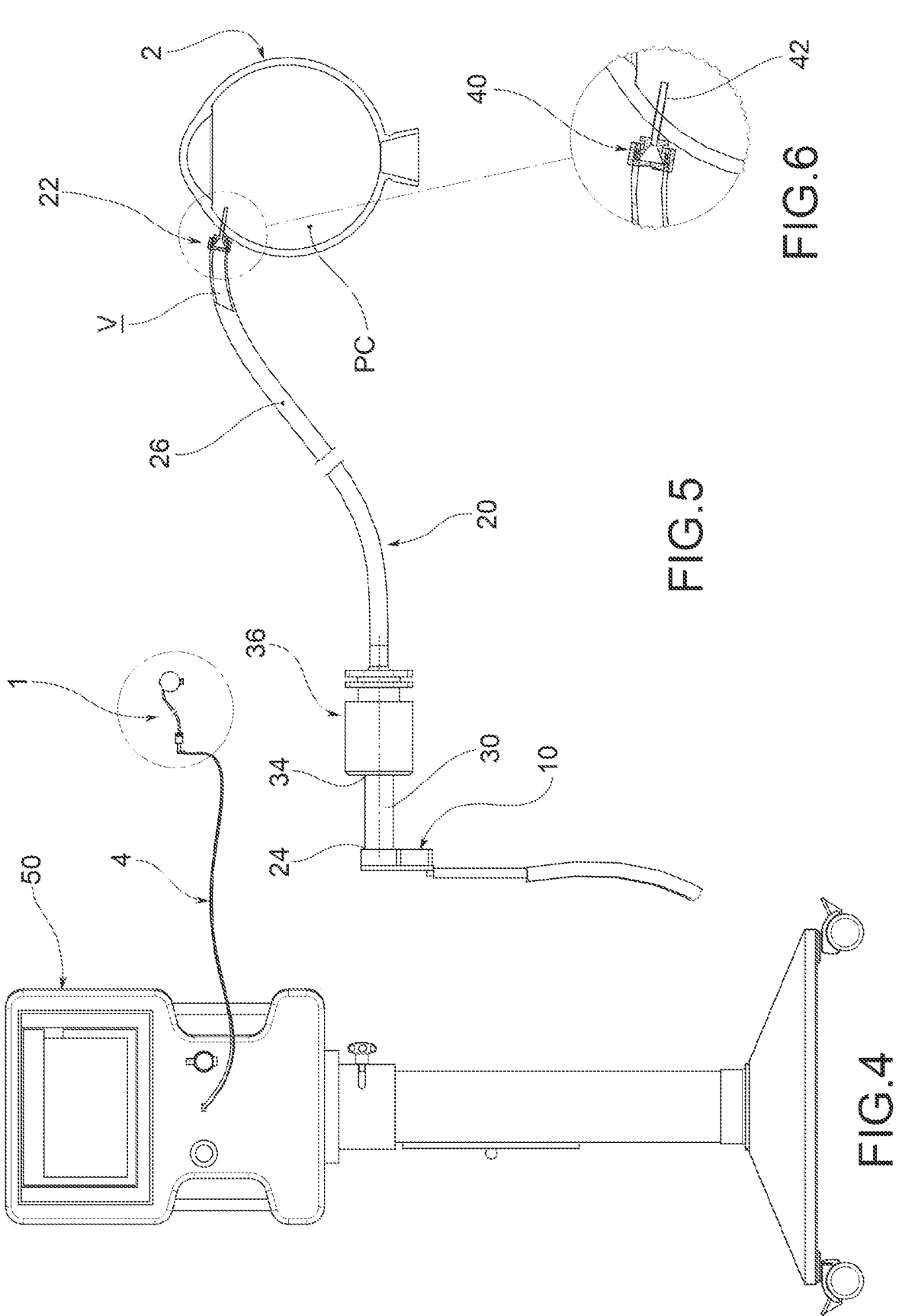
FIG. 4 shows a layout of a direct pressure detection device in an embodiment of the present invention suited for use in vitrectomy surgery, connected to a control unit.
FIG. 5 is an enlarged, partial section view of the portion in the circle in FIG. 4.
FIG. 6 is an enlarged view of the portion in the circle in FIG. 5.

The following description illustrates two possible embodiments of the invention, e.g., suitable for eye surgical procedures, cataract (FIGS. 1-3) and vitrectomy (FIGS. 4-6), respectively.

However, it is apparent that the suggested technical teaching can be applied, with possible adaptations, to other types of minimally invasive surgical procedures on the human or animal body.

In the following description, elements common to the different embodiments will be indicated by the same reference numerals.

In the drawings, a device for directly detecting pressure in a body cavity according to the present invention is referred to as 1 as a whole.

The device 1 comprises a pressure transducer 10 having a sensing surface suitable to mechanically deform by the effect of a pressure acting on it and generate an electrical voltage difference proportional to the mechanical deformation.

In an embodiment, the pressure transducer 10 is a piezo-electric transducer. In this case, the sensing surface is the surface of the piezoelectric material which generates an electrical voltage difference in response to its mechanical deformation.

The device 1 further comprises a pressure transmission device 20 suitable to transmit a change in pressure in the body cavity to the sensing surface.

For this purpose, the pressure transmission device 20 extends between a distal tip 22, suitable for partial insertion into the body cavity and a proximal port 24 in direct contact with the sensing surface of the pressure transducer 10.

The distal tip 22 thus forms an access port to place the pressure transducer 10 in fluid communication with the body cavity through the pressure transmission device 20.

In other words, in use, the distal tip 22 is suitable to be positioned through the tissue or membrane which delimits the body cavity, so that the distal end of the distal tip 22 remains within the body cavity, while the proximal end of the distal tip 22 remains outside the body cavity.

Therefore, the pressure transmission device 20 forms a volume which contains a column of air compressible or decompressible by a pressure variation of the fluid inside the body cavity, the pressure variation of the column of air being suitable to cause the mechanical deformation of the sensing surface.

In one embodiment, the proximal port 24 is fluid-tightly coupled to the sensing surface of the pressure transducer 10.

The pressure transmission device 20 comprises a flexible cannula 26 between the distal tip 22 and the proximal port 24.

The length of the flexible cannula 26 is such to allow the anchoring of an intermediate stretch thereof (i.e., between the distal tip 22 and the proximal port 24) and/or the pressure transducer 10 to which it is connected, to an anchoring zone distant from the body cavity.

For example, in the case of intraocular surgery, the anchoring zone can be a part of the patient's body, such as the chin or forehead.

In other words, the length of the flexible cannula 26 is chosen so that, in use, its distal portion comprised between the anchoring point and the body cavity is sufficiently relaxed so as not to generate significant forces at the distal tip 22 which could affect the pressure detection.

For example, the flexible cannula 26 has a minimum length of about 5-10 cm.

In an embodiment particularly suited for cataract surgical procedures, the distal tip 22 constitutes of an Anterior Chamber Maintainer 28 inserted by positive coupling and/or force coupling into a distal end portion of the flexible cannula 26.

As known, the Anterior Chamber Maintainer 28 is a cannula usually used to inject a saline solution into the anterior chamber AC of the eyeball 2. This cannula consists of a hollow needle 28' extending from a knurled bushing 28" which, in the device according to the present invention, is inserted with interference, and thereby hermetically locked, into a distal end portion of the flexible cannula 26.

For example, the knurled bushing 28" is heat-sealed to the distal end portion of the flexible cannula 26.

Therefore, in this case, at the time of the surgical procedure, the flexible cannula 26 is already equipped with the Anterior Chamber Maintainer accessory 28.

In a variant embodiment particularly suited for vitrectomy operations, the flexible cannula 26 ends distally with a trocar connector 40 suitable to connect with a trocar guide 42. Thus, the distal tip 22 consists of a trocar guide 42, free from the sharp tip, tightly coupled to the trocar connector 40.

In this case, during the surgical procedure, the sharp-tipped trocar guide 42 (known by the technical term "trocar," although sometimes this term is used to refer to the guide-tip assembly as a whole) is inserted into the body cavity, specifically the posterior PC, or vitreous, chamber of the eye, through an incision made by the sharp end of the trocar. The sharp tip is then slipped off the trocar guide 42. The latter has a proximal connecting end 42' that remains outside the body cavity to be tightly coupled to the trocar connector 40 with which the distal end of the flexible cannula 26 is provided.

In particular, the trocar connector 40 couples by overlap with the proximal connecting end 42'.

In either case, the distal tip 22 then forms a hollow tip, the distal end of which can be positioned in the anterior chamber AC or posterior chamber PC of the eyeball.

According to an embodiment, the pressure transmission device 20 comprises a transducer cannula 30 having a transducer cannula proximal end which forms the proximal port 24 and a transducer cannula distal end 34 fluidically connected to the flexible cannula 26.

In one embodiment, the transducer cannula distal end 34 is connected to the flexible cannula 26 by a connection 36, e.g., of the Luer type.

For example, the transducer cannula 30 consists of a rigid or semi-rigid tubular body to act also as a gripping element of the detection device during use.

As mentioned above, the principle of operation of the device 1 is based on the fact that the pressure transmission device 20 forms a volume V containing a column of air (or possibly another gas or gas mixture) which is either compressible or decompressible due to a variation in intracavitary pressure. The pressure variation of the air column is suitable to cause mechanical deformation of the sensing surface of the pressure transducer 10.

The flexible cannula 26, possibly connected to transducer cannula 30 forms a tubular element which is open at both ends, on one hand directly to the sensing surface of the pressure transducer and the other hand towards the distal tip, which constitutes an access port which puts the flexible cannula into communication with the inside of the body cavity.

Thus, the pressure transducer 10 is located completely outside the body cavity and only the distal tip is partially inserted into the body cavity.

Therefore, it is not necessary to insert any device inside the organ undergoing surgery.

Furthermore, the flexible cannula extended in length and thus suitable to be locked to an anchoring zone or to allow the transducer to be locked to an anchoring zone distant from the body cavity, prevents the weight of the transducer from causing a displacement of the distal tip which, even if minimal, could affect the pressure detection.

Furthermore, not having to support the transducer during the pressure detection, the operator can have both hands free.

The device 1 can be connected to an electronic control apparatus 50 only by electrical cables 4.

Therefore, the detection device 1 can be extremely light and easy to handle.

It is worth noting that in the detection device 1, a pressure variation within the body cavity is transmitted to the pressure transducer 10 through a single column of air (or other gas) into which any type of liquid (vitreous, saline, any preparation injected by the surgeon during the surgical procedure) can leak and mix without compromising the detected pressure measurement and in any case under electrically isolated conditions. The single column of air, formed by the flexible cannula 26 and any transducer cannula 30, thus effectively places the pressure transducer 10 into contact with the only access area to the body cavity through the access port formed by the distal tip. Therefore, there is no need to thread and implant anything into the body cavity and no need to make barriers or compartments in the volume which defines the individual air column.

Among other matters, since the pressure transducer and the pressure transmission device 20 are used, during the surgical procedure, completely outside the body cavity of which pressure variations are to be detected, such components of the detection device do not need to be made of materials and shapes suited for contact with the body cavity, to the advantage of simplicity and cost of production of the device.

Therefore, the detection device 1 can also detect a real-time pressure data, is an external and non-implantable device, being only in direct contact through a route to the cavity and not partitioned or compartmentalized by the cavity. For these reasons, it is applicable to minimally invasive surgery such as ophthalmic or laparoscopic surgery.

A person skilled in the art may make changes and adaptations to the embodiments of the detection device of the present invention or replace elements with others which are functionally equivalent to satisfy contingent needs without departing from the scope of protection as described and claimed herein. All the features described above as belonging to a possible embodiment may be implemented independently of the other described embodiments.

What is claimed is:

1. A device configured for directly detecting pressure variations of a fluid within a body cavity, in particular in an anterior eye chamber or a posterior eye chamber, the device comprising:
   a pressure transducer having a sensing surface suitable to mechanically deform by effect of a pressure acting on the sensing surface and generate an electrical voltage difference proportional to mechanical deformation,
   a proximal port in direct contact with the sensing surface of the pressure transducer,
   a distal tip configured for partial insertion into the body cavity,
   a pressure transmission device extending between the distal tip and the proximal port,
   wherein the pressure transmission device forms a volume that contains a column of gas, the pressure variation of the column of gas configured to cause the mechanical deformation of the sensing surface,
   wherein the distal tip is configured to form an access port that places the pressure transducer into direct fluid communication with the inside of the body cavity when the distal tip is partially inserted into the body cavity; and
   wherein the pressure transmission device comprises, between the distal tip and the proximal port, a flexible cannula having a length, wherein the length is sufficient to allow, when in use, a distal portion of the flexible cannula between the body cavity and an anchoring zone distant from the body cavity to be sufficiently relaxed so as not to generate significant forces at the distal tip which could affect pressure detection, and wherein the length is sufficient to prevent, when in use, displacement of the distal tip by the weight of the pressure transducer.

2. The device of claim 1, wherein the distal tip comprises an anterior chamber maintainer inserted by positive coupling and/or force coupling into a distal end portion of the flexible cannula.

3. The device of claim 1, wherein the flexible cannula distally terminates with a trocar connector, and wherein the distal tip consists of a trocar guide tightly coupled to and overlapped by the trocar connector.

4. The device of claim 1, wherein the pressure transmission device comprises a transducer cannula comprising a transducer cannula proximal end forming the proximal port and a transducer cannula distal end fluidically connected to the flexible cannula.

5. The device of claim 4, wherein the transducer cannula distal end is connected to the flexible cannula by a connection.

6. The device of claim 5, wherein the connection is a Luer type connection.

7. The device of claim 1, wherein the pressure transducer is a piezoelectric transducer.

8. The device of claim 7, wherein the pressure transmission device comprises a transducer cannula comprising a transducer cannula proximal end forming the proximal port and a transducer cannula distal end fluidically connected to the flexible cannula, and wherein the piezoelectric transducer has a sensing surface that extends predominantly on a plane substantially orthogonal to an axis of the transducer cannula.

9. The device of claim 4, wherein the transducer cannula comprises a rigid or semi-rigid tubular body configured to act also as a gripping element of the device during use.

10. The device of claim 1, wherein said gas is compressible or decompressible by a pressure variation of the fluid inside the body cavity.

11. The device of claim 1, wherein said gas is air.

12. A device configured for directly detecting pressure variations of a fluid within a body cavity, the device comprising:

a pressure transducer having a sensing surface configured to mechanically deform by effect of a pressure acting on the sensing surface and configured to generate an electrical voltage difference proportional to the mechanical deformation of the sensing surface, a proximal port in direct contact with the sensing surface of the pressure transducer, a distal tip configured for partial insertion into a body cavity, a pressure transmission device extending between the distal tip and the proximal port, wherein the pressure transmission device forms a volume that contains a column of gas, the pressure variation of the column of gas configured to cause the mechanical deformation of the sensing surface, wherein the distal tip is configured to form an access port that places the pressure transducer into direct fluid communication with the inside of the body cavity when the distal tip is partially inserted into the body cavity; and wherein the pressure transmission device comprises, between the distal tip and the proximal port, a flexible cannula having a length of 5 cm or more, the flexible cannula comprising a distal portion connected to the distal tip and further comprising an intermediate stretch configured to be anchored to an anchoring zone.

13. The device of claim 12, further comprising a connection between the pressure transmission device and the proximal port.

14. The device of claim 13, wherein the pressure transducer comprises a transducer cannula between the connection and the proximal port.

15. The device of claim 12, wherein the proximal port is fluid-tightly coupled to the sensing surface of the pressure transducer.

16. The device of claim 12, wherein the flexible cannula has a length of 10 cm or more.

* * * * *